(12) United States Patent
Urano et al.

(10) Patent No.: US 7,679,073 B2
(45) Date of Patent: Mar. 16, 2010

(54) MEDICAL DEVICE

(75) Inventors: Susumu Urano, Hiroshima (JP); Shuji Kaneko, Hiroshima (JP); Seinoshin Hamanaka, Minato-ku (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 223 days.

(21) Appl. No.: 11/826,964

(22) Filed: Jul. 19, 2007

(65) Prior Publication Data
US 2008/0197304 A1 Aug. 21, 2008

(30) Foreign Application Priority Data
Feb. 16, 2007 (JP) .............. 2007-036352

(51) Int. Cl.
*A61N 5/10* (2006.01)
(52) U.S. Cl. .............. 250/505.1; 250/492.3; 250/515.1; 315/502; 378/112
(58) Field of Classification Search .............. 250/492.3, 250/505.1, 515.1; 315/502; 376/112
See application file for complete search history.

(56) References Cited

U.S. PATENT DOCUMENTS

| | | | |
|---|---|---|---|
| 7,303,334 B2 * | 12/2007 | Cadwalader et al. | ........ 378/203 |
| 7,491,590 B2 * | 2/2009 | Maekawa | ................... 438/158 |
| 2004/0113099 A1 * | 6/2004 | Eickhoff et al. | .......... 250/492.3 |
| 2006/0153330 A1 | 7/2006 | Wong et al. | |
| 2006/0245537 A1 | 11/2006 | Bakai et al. | |
| 2009/0200483 A1 * | 8/2009 | Gall et al. | ............... 250/396 R |

FOREIGN PATENT DOCUMENTS

| EP | 1 419 801 A1 | 5/2004 |
|---|---|---|
| JP | 60-33970 Y2 | 10/1985 |
| JP | 6-26811 U | 4/1994 |
| JP | 9-140700 A | 6/1997 |
| JP | 9-149899 A | 6/1997 |
| JP | 10-71213 A | 3/1998 |
| JP | 10-511595 A | 11/1998 |
| JP | 11-151236 A | 6/1999 |
| JP | 3033679 B2 | 4/2000 |
| JP | 2001-269332 A | 10/2001 |
| JP | 2003-000582 A | 1/2003 |
| JP | 2005-522257 A | 7/2005 |
| JP | 2006-006471 A | 1/2006 |
| JP | 2006-21046 A | 1/2006 |

(Continued)

OTHER PUBLICATIONS

Kamino et al., Int. J. Radiation Oncology Biol. Phys., vol. 66, No. 1, pp. 271-278, 2006.

*Primary Examiner*—David A Vanore
(74) *Attorney, Agent, or Firm*—Birch, Stewart, Kolasch & Birch, LLP

(57) ABSTRACT

A medical device can perform treatment and diagnosis without causing a sense of unease to the patient. The medical device includes a substantially ring-shaped support frame provided in such a manner that a central axis through which an isocenter passes is disposed substantially horizontally; a substantially ring-shaped moving gantry which slides relative to the support frame and which has an opening at the isocenter side thereof a radiation emitter configured to emit a beam towards the isocenter; and a protective cover which covers the radiation emitter and an inner circumferential side of the moving gantry and which moves together with the moving gantry.

8 Claims, 5 Drawing Sheets

FOREIGN PATENT DOCUMENTS

| | | |
|---|---|---|
| JP | 2006-25894 A | 2/2006 |
| WO | WO 94/28971 A2 | 12/1994 |
| WO | WO-97/13552 A1 | 4/1997 |
| WO | WO-00/74779 A1 | 12/2000 |
| WO | WO-03/086192 A1 | 10/2003 |
| WO | WO-2005/053794 A1 | 6/2005 |
| WO | WO-2006/061772 A2 | 6/2006 |

* cited by examiner

MEDICAL DEVICE

BACKGROUND OF THE INVENTION

1. Field of the Invention

The present invention relates to medical devices, for example, radiotherapy apparatuses and CT (computed tomography) apparatuses.

2. Description of Related Art

Stereotactic radiotherapy apparatuses are known medical devices for performing treatment by irradiating an affected area, such as a tumor, with radiation. Such Stereotactic radiotherapy apparatuses emit radiation a plurality of times in multiple directions towards the same affected area. To emit radiation from multiple directions, it is necessary to dispose a radiation emitter at a position corresponding to a location for emitting the radiation for irradiating the affected area, and to allow the radiation detector to be moved to a plurality of positions around the patient and aligned. Known approaches for moving the radiation emitter in this way include the cantilever type, robotic arm type, and gantry type approaches.

In the cantilever type approach, the radiation emitter is supported in a cantilevered manner and rotated around the patient's body. In the robotic arm type approach, the radiation emitter is attached to the end of a multi-axis arm, and the radiation is emitted from an arbitrary direction. However, with the cantilever type approach or the robotic arm type approach, because of a structure for attaching the radiation emitter to the end of the cantilever or the arm, the cantilever or the arm becomes deformed due to the weight of the radiation emitter, thus making high-precision positioning (setting the irradiation direction) difficult.

In contrast, in the gantry type approach, a gantry is positioned so as to surround a patient lying on a couch, and the radiation emitter is moved along the gantry or together with the gantry. The gantry type approach is a preferable structure for realizing high-precision positioning because the radiation emitter is supported by a highly rigid gate-shaped gantry. Medical devices using this gantry type approach have been disclosed, for example, in Japanese Translation of PCT International Application, Publication No. HEI-10-511595, which is related to a radiotherapy apparatus described below, and Japanese Unexamined Patent Application, Publication No. HEI-10-71213, which is related to a proton-beam therapy apparatus.

With the cantilever type approach and the gantry type approach, to increase the degrees of freedom of the irradiation direction, positioning control (translation and rotation) of the couch on which the patient is set is performed, in addition to movement of the radiation emitter in a single direction.

BRIEF SUMMARY OF THE INVENTION

However, with the medical devices disclosed in Japanese Translation of PCT International Application, Publication No. HEI-10-511595 and Japanese Unexamined Patent Application, Publication No. HEI-10-71213, the radiation emitters which protrude towards the patient are rotated close to the patient, thus causing the patient to experience a sense of unease, which is undesirable.

The present invention has been conceived in light of the circumstances described above, and an object thereof is to provide a medical device which can perform treatment and diagnose patient without causing him or her to experience a sense of unease.

To solve the problems described above, the medical device of the present invention provides the following solutions.

The medical device according to the present invention comprises a substantially ring-shaped support frame provided in such a manner that a central axis through which an isocenter passes is disposed substantially horizontally; a substantially ring-shaped moving gantry which slides relative to the support frame and which has an opening at the isocenter side thereof; a radiation emitter configured to emit a beam towards the isocenter; and a protective cover which covers the radiation emitter and an inner circumferential side of the moving gantry and which moves together with the moving gantry.

Because the protective cover covers the radiation emitter, the patient is not given the impression that the radiation cover is protruding towards him or her, looming close, and therefore, the patient does not experience a sense of unease.

Here, the term moving means rotation of moving gantry in any direction about a central axis extending substantially horizontally, and includes both continuous rotation and rotation by an arbitrary angle.

In the medical device according to the present invention, the protective cover may have an opening defined by opposing portion configured to cover the radiation emitter and side portions disposed at both sides of the opposing portion as viewed from the central axis; and a distance from the central axis to the side portions is longer than a distance from the central axis to the opposing portion.

Because the protective cover includes the side portions whose distance from the central axis is greater than for the opposing portion, a large space is formed toward the inside from these side portions. Therefore, even when the patient is placed inside the opening, it is possible to ensure a large working space, and the ease of use during a procedure carried out by the operator, for example, for aligning the affected area of the patient with respect to the isocenter can thus be improved.

Also, because a large space is formed toward the inside from the side portions, when placing the patient inside the opening, it is possible to reduce the sense of unease and the feeling of confinement of the patient.

Furthermore, by using the large space formed at the side portions, it is possible to radiate laser light or infrared light for checking the alignment of the affected area. Therefore, it is possible to ensure a large scanning range for the laser light or infrared light.

In the medical device according to the present invention, the side portions may include flat portions.

Because the flat portions are provided, the operator can place his or her hand on the flat portion during operation to take some of his or her weight, thus improving the ease of use. This is particularly effective when the flat portion is positioned horizontally.

In the medical device according to the present invention, a patient-introducing mode may be provided, wherein the side portion of the protective cover may be positioned in the viewing direction of a patient when the patient is introduced inside the opening of the protective cover.

When the patient is introduced inside the circular track, the side portion is located in the viewing direction of the patient. Therefore, a large space is formed in the viewing direction of the patient, allowing the sense of unease and the feeling of confinement of the patient to be further reduced.

In the medical device according to the present invention, an outside cover which is fixed to the support frame may be provided at the outer side of the protective cover.

By positioning the outside cover relative to outside of the protective cover, there is no contact with the moving devices (such as the radiation emitter) in the medical device, thus improving safety. Also, because direct eye contact with components can be avoided, it is possible to reduce the sense of unease of the patient when inserted into the opening. Furthermore, providing the outside cover accommodates the internal devices of the medical device together with the protective cover. Accordingly, as well as preventing deterioration of the soundness of the internal devices by preventing the ingress of foreign objects or moisture, it is also possible to ensure safety in the event that internal devices fall off, for example.

In the medical device according to the present invention, the protective cover may be divided into at least two parts.

Because the protective cover can be removed in parts, it is not necessary to remove the entire protective cover during maintenance or inspection. For example, if it is possible to partially remove the opposing portion corresponding to the radiation emitter, which requires frequent maintenance, the maintenance work or inspection work can be significantly simplified.

In the medical device according to the present invention, a safety switch may be provided on the protective cover.

Because a safety switch is provided on the protective cover, it is possible to stop the medical device in the event of contact with a person or an object, for any reason, which allows accidents to be avoided. Examples of such contact include contact between the patient and the medical device during motion of moving and rotation.

The present invention provides the following advantages.

Because protrusion of the radiation emitter into the space where the patient is setting is eliminated by the shape of the protective cover and the space is increased as much as possible, it is possible to avoid giving the patient the impression that the radiation emitter is protruding towards him or her, looming in, and it is thus possible to reduce the sense of unease experienced by the patient.

DETAILED DESCRIPTION OF THE INVENTION

An embodiment of the present invention will be described below with reference to the drawings.

First, the concept of the radiotherapy apparatus according to this embodiment will be described, and then a detailed description of all matters relating to the present invention will be given.

Figure 1:
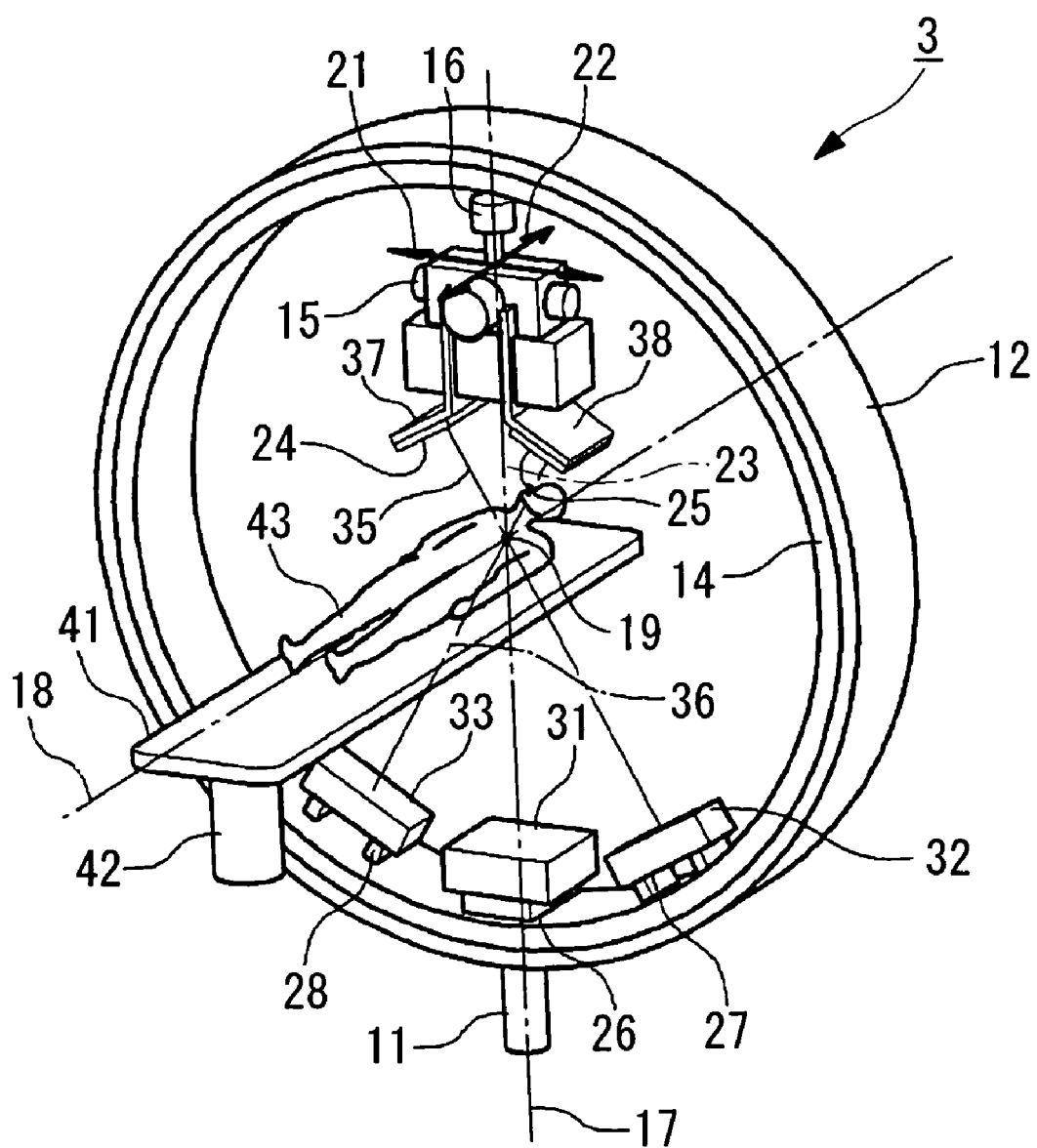
FIG. 1 is a schematic perspective view conceptually illustrating a radiotherapy apparatus according to an embodiment of the present invention.

FIG. 1 shows a schematic perspective view of a radiotherapy apparatus 3 according to this embodiment. The radiotherapy apparatus (medical device) 3 includes a rotary driving device 11, a support frame 12, a moving gantry 14, a swinging mechanism 15, and a therapeutic-radiation irradiating device (radiation emitter) 16.

The rotary driving device 11 supports the support frame 12 in such a manner as to allow rotation about a rotation axis 17 which extends substantially vertically. In other words, the support frame 12 is supported at one position by only the rotary driving device 11 located therebelow. Control of rotation by the rotary driving device 11 is performed by a radiotherapy-apparatus control unit (not shown in the drawing).

As used here, the term rotation means the rotary motion of support flame in any direction about an axis that extends vertically and includes either continuous rotation or rotation by an arbitrary angle.

The support frame 12 is substantially ring shaped having an opening at the center. The support frame 12 in the present invention is not limited to a ring shape, however. It may be a rectangular shape with an opening provided at the center. The shape is preferably determined from the viewpoint of stability (as the center of gravity becomes lower, the stability increases), structural soundness (deformability), space required for rotation of the support frame 12, and so forth.

The support frame 12 is installed such that a central axis 18 thereof is positioned substantially horizontally. The moving gantry 14 is supported to the support frame 12 in such a manner as to be capable of moving along the support frame 12. The moving gantry 14 moves about the central axis 18 of the support frame 12 along circular tracks (not shown in the drawing) provided on both sides of the support frame 12. The intersection of the central axis 18, serving as the center for the motion of the moving gantry 14, and the rotation axis 17 of the support frame 12 corresponds to an isocenter 19. Revolving control of the moving gantry 14 is performed by the radiotherapy-apparatus control unit (not shown in the drawings).

As used here, the terms moving means rotation of moving gantry in any direction about a central axis that extends substantially horizontally and includes either continuous rotation or rotation by an arbitrary angle.

The swinging mechanism 15 is fixed at the inner circumference side of the moving gantry 14 and supports the therapeutic-radiation irradiating unit 16 in such a manner as to be capable of move of rotation. The swinging mechanism 15 has a pan axis 21 and a tilt axis 22. The pan axis 21 is fixed with respect to the moving gantry 14 and is orthogonal to the central axis 18 of the support frame 12. The tilt axis 22 is fixed with respect to the moving gantry 14 and is orthogonal to the pan axis 21. The swinging mechanism 15 is controlled by the radiotherapy-apparatus control unit (not shown in the drawings), which rotates the therapeutic-radiation irradiating device 16 about the pan axis 21 and about the tilt axis 22. Thus, the therapeutic-radiation irradiating device 16 radiates therapeutic radiation 23 at a controlled radiation angle.

The therapeutic-radiation irradiating device 16 includes an accelerator, a radiation conversion target, and a multi-leaf collimator (none of which are shown in the drawing) in this order from the top to the bottom in FIG. 1. An electron beam accelerated in the accelerator is incident on the radiation conversion target, causing bremsstrahlung (X-ray) to be emitted. This bremsstrahlung is shaped at openings defined by the multi-leaf collimator so as to have a shape prescribed by a treatment plan. Generally, a fixed collimator, a flattening filter and so forth are also disposed between the radiation conversion target and the multi-leaf collimator. Normally, a linear accelerator is used as the accelerator because of its compactness and lightness. To reduce the overall size and weight, its constitutional elements are arranged in series along the electron-beam acceleration direction of the linear accelerator (the central axis of the accelerator). The therapeutic-radiation irradiating device 16 is disposed so that this acceleration direction points towards the isocenter 19. Therefore, the therapeutic-radiation irradiating device 16 is disposed so as to present a protruding shape, which protrudes towards the isocenter 19 in the substantially ring-shaped moving gantry 14.

Because the therapeutic-radiation irradiating device 16 is supported on the moving gantry 14 which moves with respect to the support frame 12, once the therapeutic-radiation irradiating device 16 is temporarily adjusted so that it points towards the isocenter 19, even if the support frame 12 rotates or the moving gantry 14 moves, the therapeutic radiation 23 always passes substantially through the isocenter 19.

The radiotherapy apparatus 3 also includes a plurality of imager systems. More specifically, the radiotherapy apparatus 3 includes radiation-source driving devices 37 and 38, diagnostic X-ray sources 24 and 25, sensor-array driving devices 27 and 28, and sensor arrays 32 and 33.

The radiation-source driving device 37 is fixed to the inner circumference side of the moving gantry 14 and supports the diagnostic X-ray source 24 relative to the moving gantry 14. The radiation-source driving device 37 is controlled by the radiotherapy-apparatus control unit (not shown in the drawing) to move the diagnostic X-ray source 24 relative to the moving gantry 14. The diagnostic X-ray source 24 is disposed at the inner circumference side of the moving gantry 14 and is disposed at a position such that an angle formed by the line joining the isocenter 19 and the diagnostic X-ray source 24 and a line joining the isocenter 19 and the therapeutic-radiation irradiating device 16 is an acute angle. The diagnostic X-ray source 24 is controlled by the radiotherapy-apparatus control unit (not shown in the drawing) to radiate diagnostic X-ray 35 towards the isocenter 19. The diagnostic X-ray 35 is radiated from one point of the diagnostic X-ray source 24 and forms a circular cone-shaped beam with the one point at the apex.

The radiation-source driving device 38 is fixed to the inner circumference side of the moving gantry 14 and supports the diagnostic X-ray source 25 relative to the moving gantry 14. The radiation-source driving device 38 is controlled by the radiotherapy-apparatus control unit (not shown in the drawing) to move the diagnostic X-ray source 25 relative to the moving gantry 14. The diagnostic X-ray source 25 is disposed at the inner circumference side of the moving gantry 14 and is disposed at a position such that an angle formed by a line joining the isocenter 19 and the diagnostic X-ray source 25 and a line joining the isocenter 19 and the therapeutic-radiation irradiating device 16 is an acute angle. The diagnostic X-ray source 25 is controlled by the radiotherapy-apparatus control unit (not shown in the drawing) to radiate diagnostic X-ray 36 towards the isocenter 19. The diagnostic X-ray 36 are radiated from one point on the diagnostic X-ray source 25 and form a circular cone-shaped beam having the one point at the apex thereof.

The sensor-array driving device 27 is fixed to the inner circumference side of the moving gantry 14 and supports the sensor array 32 with respect to the moving gantry 14. The sensor-array driving device 27 is controlled by the radiotherapy-apparatus control unit (not shown in the drawing) to move the sensor array 32 relative to the moving gantry 14.

The sensor-array driving device 28 is fixed to the inner circumference side of the moving gantry 14 and supports the sensor array 33 relative to the moving gantry 14. The sensor-array driving device 28 is controlled by the radiotherapy-apparatus control unit (not shown in the drawing) to move the sensor array 33 relative to the moving gantry 14.

The sensor array 32 receives the diagnostic X-ray 35 radiated by the diagnostic X-ray source 24 and passing through the subject around the isocenter 19, and generates a transmission image of the subject.

The sensor array 33 receives the diagnostic X-ray 36 radiated by the diagnostic X-ray source 25 and passing through the subject around the isocenter 19, and generates a transmission image of the subject.

The sensor arrays 32 and 33 may be, for example, FPDs (flat panel detectors) or X-ray I.I.s (image intensifiers).

With this imager system, even if the diagnostic X-ray sources 24 and 25 are moved by the radiation-source driving devices 37 and 38, respectively, the sensor arrays 32 and 33 can suitably moved by the sensor-array driving devices 27 and 28 and generate transmission images centered on the isocenter 19.

The radiotherapy apparatus 3 also includes a sensor-array driving device 26 and a sensor array 31. The sensor-array driving device 26 is fixed to the inner circumference side of the moving gantry 14 and supports the sensor array 31 relative to the moving gantry 14. The sensor-array driving device 26 is controlled by the radiotherapy-apparatus control unit (not shown in the drawing) to move the sensor array 31 relative to the moving gantry 14. The sensor array 31 receives the therapeutic radiation 23 radiated by the therapeutic-radiation irradiating device 16 and passing through the subject around the isocenter 19, and generates a transmission image of the subject. The sensor array 31 may be, for example, an FPD (flat panel detector) or an X-ray I.I. (image intensifier). Even if the therapeutic-radiation irradiating device 16 is moved by the swinging mechanism 15, the sensor array 31 can suitably moved by the sensor-array driving device 26 and generate a transmission image centered on the isocenter 19.

The diagnostic X-ray source 24 can also be disposed at a position such that the angle formed by the line joining the isocenter 19 and the diagnostic X-ray source 24 and a line joining the isocenter 19 and the therapeutic-radiation irradiating device 16 is an obtuse angle. In other words, the sensor array 32 is disposed at a position such that the angle formed by the line joining the isocenter 19 and the sensor array 32 and the line joining the isocenter 19 and the therapeutic-radiation irradiating device 16 is an acute angle.

Similarly, the diagnostic X-ray source 25 can also be disposed at a position such that the angle formed by the line joining the isocenter 19 and the diagnostic X-ray source 25 and the line joining the isocenter 19 and the therapeutic-radiation irradiating device 16 is an obtuse angle. In other words, the sensor array 33 is disposed at a position such that the angle formed by the line joining the isocenter 19 and the sensor array 33 and the line joining the isocenter 19 and the therapeutic-radiation irradiating device 16 is an acute angle.

Disposing them in this way is preferable from the viewpoint of protecting the devices, because it is difficult for the sensor arrays 32 and 33 to be irradiated with the therapeutic radiation 23 radiated from the therapeutic-radiation irradiating device 16.

It is also possible for the radiation-source driving devices 37 and 38 to respectively support the diagnostic X-ray sources 24 and 25 relative to the therapeutic-radiation irradiating device 16. Even if the therapeutic-radiation irradiating device 16 is moved by the swinging mechanism 15 at this time, the radiotherapy apparatus 3 affords an advantage in that the relative position with respect to the therapeutic-radiation irradiating device 16 is fixed, and the position of the diagnostic X-ray sources 24 and 25 is more easily controlled.

A couch 41 is used for setting the patient 43 being treated. The couch 41 includes a restrainer (not shown). This restrainer restrains the patient 43 on the couch 41 so that the patient 43 does not move. A couch-driving device 42 supports the couch 41 on a base and is controlled by the radiotherapy-apparatus control unit (not shown in the drawing) to move the couch 41 so that it is guided inside the opening in the support frame 12.

Figure 2:
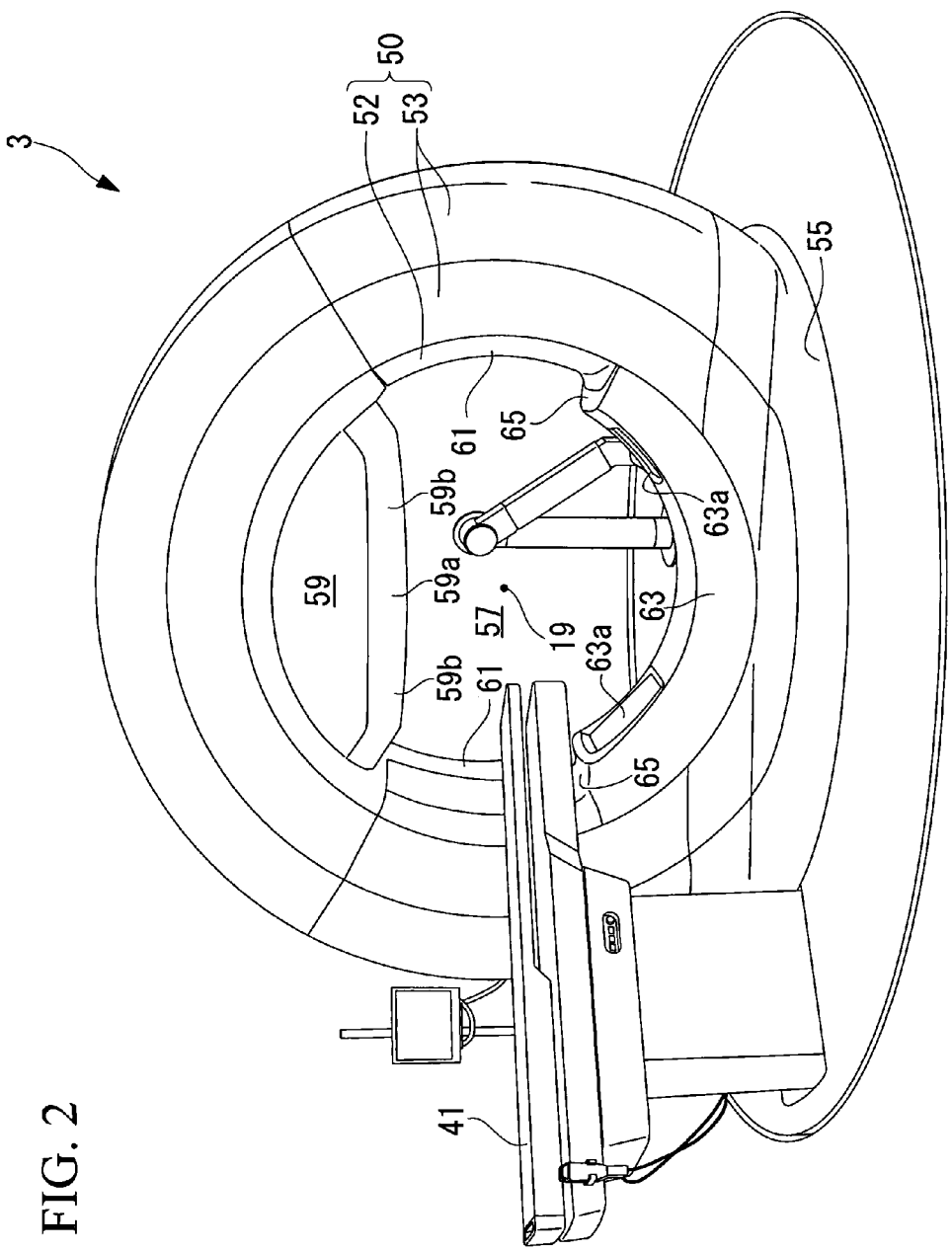
FIG. 2 is a perspective view showing a radiotherapy apparatus on which a cover is installed.

FIG. 2 is a perspective view showing a cover 50 provided on the radiotherapy apparatus 3.

The cover 50 includes a protective cover 52 disposed on the inner circumference side and an outside cover 53 disposed on the outer circumference side of the protective cover 52. Each structure shown in FIG. 1 is contained inside a space enclosed by the protective cover 52 and the outside cover 53.

A rotating floor 55 is disposed below the cover 50. The rotating floor 55 is fixed relative to the support frame 12 so as to allow it to rotate about the rotation axis 17 in conjunction with the rotation performed by the rotary driving device 11. A lower end portion of the outside cover 53 is fixed with respect to the rotating floor 55. Therefore, the outside cover 53 rotates together with the rotating floor 55.

The protective cover 52 is configured such that an opening 57 is formed at the central part thereof. That is, the protective cover 52 extends over 360° as viewed from the isocenter 19.

The protective cover 52 is fixed to the moving gantry 14. Therefore, the protective cover 52 moves about the central axis 18 in conjunction with the motion of the moving gantry 14. The protective cover 52 is separated from the outside cover 53. Therefore, the outside cover 53 maintains a fixed position independent of the motion of the moving gantry 14. In other words, the protective cover 52 and the outside cover 53 move relative to each other, with respect to that motion. Therefore, to ensure safety for avoiding things becoming caught between the protective cover 52 and the outside cover 53, and to ensure soundness of the apparatus by preventing foreign objects, liquid, or the like getting inside the cover 50, the gap between the joining surfaces thereof is preferably minimized, preferably by providing a structure for overlapping them with each other by folding back the ends thereof.

The protective cover 52 includes a radiation cover portion 59 for housing the therapeutic-radiation irradiating device 16 and devices in its vicinity, side cover portions 61 disposed at both sides of the radiation cover portion 59, and a sensor cover portion 63 which is disposed opposite the radiation cover portion 59 and which houses the sensor arrays 31, 32, 33, and so forth.

The radiation cover portion 59 includes an opposing portion 59a disposed opposite the therapeutic-radiation irradiating device 16 and neighboring portions 59b disposed at both sides of the opposing portion 59a as viewed from the isocenter 19. The position of the opposing portion 59a is determined by the distance between the isocenter 19 and the radiation conversion target and by the total length of the component elements in the therapeutic-radiation irradiating device 16, from the radiation conversion target onwards. The patient 43 is disposed inside the opening 57 after he or she lies on its side on the couch 41. To reduce the patient's feeling of confinement at this time as much as possible, it is preferable to increase the space inside the opening 57 as much as possible. In this case, the opposing portion 59a has the minimum distance from the isocenter 19.

The opposing portion 59a and the neighboring portions 59b are arranged substantially in a straight line. In other words, the opposing portion 59a and the neighboring portions 59b form a surface hiding the protruding shape of the therapeutic-radiation irradiating device 16, which protrudes towards the isocenter 19. Thus, because the protective cover 52 covers the radiation emitter, the patient is not given the impression that the radiation emitter protrudes towards him or her, looming close, and therefore the patient is not made to feel uneasy.

As for the distance from the isocenter 19, each of the side cover portions 61 is larger from the radiation cover portion 59. Therefore, it is possible to form a large space at the inner sides of the side cover portions 61. More specifically, when the patient 43 is placed inside the opening 57, it is possible to increase the working space for the operator to perform the procedure for positioning the affected part of the patient 43 at the isocenter 19. By increasing the working space therefor, it is possible to improve the ease of use of the operator, to improve the positioning precision by ensuring sufficient viewing area for the operator to confirm the reasonable positioning, and to eliminate set-up errors (or to reduce set-up errors) caused by contact between the operator and the couch during positioning.

Openings 63a are formed in the sensor cover portion 63 at the detection side of the sensor arrays 32 and 33. Acrylic sheets (not shown) having a substantially uniform thickness are preferably disposed in the openings 63a to protect the sensor arrays 32 and 33. In general, the cover 50 of the medical device has a curved shape, and therefore, a manufacturing step for controlling the thickness of the cover 50 to make it substantially uniform is not performed. However, when diagnostic X-ray is detected through the cover 50 by a sensor array which relatively moves about the central axis with respect to the cover 50, it is not possible to obtain accurate information because attenuation of the X-rays in the cover differs depending on position. One approach to eliminate this effect is to divide the cover 50 into at least two parts at a plane orthogonal to the central axis 18, join the connection portions thereof with a member having substantially uniform thickness, and detect the X-rays through this uniform-thickness member. In such a case, if the cover 50 is fixed, by disposing the uniform-thickness member around the entire circumference, the strength of the cover 50 itself is reduced. However, as in this embodiment, by using a structure in which the openings 63a are provided in the protective cover 52, which moves together with the moving gantry 14, it is possible to detect the diagnostic X-ray passing through the patient 43 with low attenuation, without being affected by the thickness distribution of the cover 50. Because this does not require the thickness of the cover 50, which has a curved shaped, to be controlled so as to be substantially constant, it is possible to manufacture the cover 50 at low cost.

The sensor cover portion 63 moves in conjunction with the moving operation of the gantry 14. Therefore, it is possible to support detection of the diagnostic X-ray at any moving angle with large sensor arrays, from the viewpoint of ensuring sufficient structural strength of the cover 50. This means that it is possible to detect diagnostic X-ray high resolution over a large surface area, and therefore, it is possible to evaluate a wide region including the image-acquisition target site (affected area etc.) using a single image acquisition.

The side cover portions 61 include flat portions 65 at the boundaries with the sensor cover portion 63. Therefore, during a procedure, the operator can place his or her hand on this flat portion 65 to receive some of his or her weight, which allows the ease of use to be improved. An example of this procedure carried out by the operator is aligning the affected area of the patient at the isocenter. This is particularly effective when the flat portion 65 is positioned horizontally, as shown in FIG. 2.

The radiation cover portion 59, the side cover portions 61, and the sensor cover portion 63 described above can be individually removed from the main body of the protective cover 52. More preferably, part of each of the cover portions 59, 61, and 62 can be removed. From the viewpoint of improving ease of use and preventing the removed part from falling off, it is preferable to position each removable part with respect to the cover using a locating pin, a hook and loop fastener such as Velcro fastener (registered trademark), a magnet or the like. By enabling partial removal in this way, it is not necessary to remove the entire cover 50 during maintenance. For example, because the multi-leaf collimator of the therapeutic-radiation irradiating device 16 is used in a radiation environment, the lifetime of a motor for driving the leaves (not shown in the drawing) is particularly short. Therefore, it is necessary to maintain and inspect these parts frequently. By enabling partial removal of the radiation cover portion 59, it is possible to simplify the maintenance and inspection work, and it is thus possible to reduce the time required.

Figure 3A:
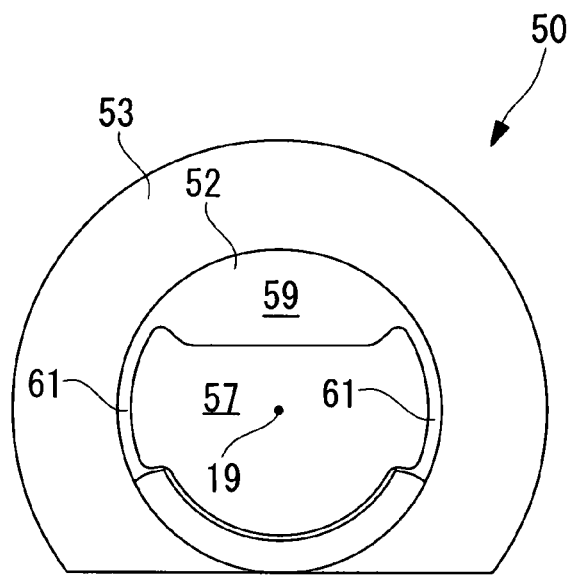
FIG. 3A is a front elevational view of the cover showing a state in which a radiation cover portion of a protective cover is disposed at the top.
Figure 3B:
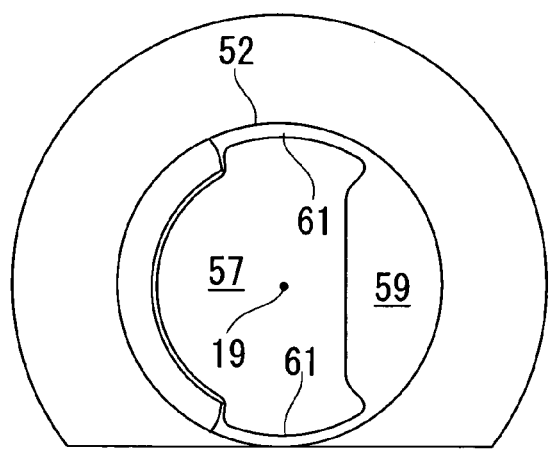
FIG. 3B is a front elevational view of the cover showing a state in which a side cover portion of the protective cover is disposed at the top.

FIG. 3A and FIG. 3B show front elevational views of the cover 50. These figures correspond to parts located above the rotating floor 55. As shown in FIG. 3A, the radiation cover portion 59 is positioned directly above the isocenter 19, and the state having the minimum distance from the isocenter relative to the rotation axis 17 direction is defined as a reference state. FIG. 3B shows a state in which the protective cover 52 is rotated by 90° clockwise relative this reference state. In this state, by positioning the side cover portions 61 vertically, a large space is formed in the vertical direction. A large space is formed at the top, which is preferable because it reduces the sense of confinement of the patient lying on the couch 41 when guiding him or her into the opening 57. So, when such a mode for positioning the side cover portion 61 at the top is provided, known as a patient-introducing mode, it is possible to reduce the sense of unease experienced by the patient.

As shown in FIG. 3B, in the state where the side cover portion 61 is positioned at the top, by using the large upper space that is formed, it is possible to irradiate laser light or infrared light for checking the position of the affected area. Therefore, it is possible to ensure a large scanning range for this laser light or infrared light. This is beneficial in cases where the laser light or infrared light is radiated from a laser light source or infrared light source fixed to the ceiling of the room where the radiotherapy apparatus 3 is installed, for example, when carrying out rough positioning before conducting diagnosis of the affected area using the diagnosis X-ray sources 24 and 25.

The rotation range of the cover 50 by the rotary driving device 11 is set as follows for avoiding contact with the patient lying on the couch 41.

The rotation range of the cover 50 is determined according to the position of the protective cover 52, which moves together with the moving gantry 14. In other words, as shown in FIG. 3A, when the side cover portions 61 are positioned at both sides of the isocenter 19 (that is, at both sides of the patient lying on the couch 41), the rotation range of the cover 50 is set so as to increase; and as shown in FIG. 3B, when the radiation cover portion 59, which has the smallest distance from the isocenter 59, is positioned at the side of the isocenter (that is, at the side of the patient lying on the couch 41), the rotation range is set to as to decrease. By determining the rotation range of the cover 50 according to the position of the protective cover 52 in this way, it is possible to operate the apparatus safely without the patient making contact with the radiation cover portion 59 of the protective cover 52.

The relationship between the position of the protective cover 52 and the rotation range of the cover 50 may be stored in advance in a database and then referred to.

The radiotherapy apparatus 3 according to this embodiment includes safety switches which can safely halt the operation of the radiotherapy apparatus 3 in the event that the patient, the operator, or an object makes contact with the cover 50. The sensors used in these safety switches may be contact type sensors or non-contact type sensors. For example, it is possible to use touch sensors, ultrasonic sensors, infrared sensors or the like. Also, the sensors used in the safety switches are preferably flat so as to enable a prescribed sensing area to be ensured.

Figure 4:
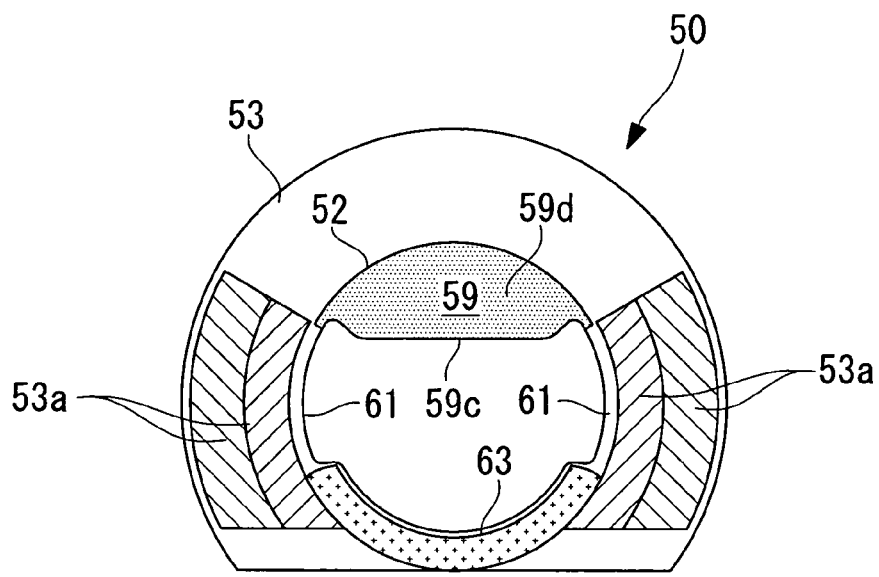
FIG. 4 is a front elevational view showing the position of safety switches provided on the cover.

FIG. 4 shows a concrete example in which safety switches are provided in each portion of the cover 50. A safety switch for detecting contact with the patient when, for example, the cover 50 rotates is provided on an inner circumference edge 59c of the radiation cover portion 59.

On an outer circumferential portion 59d, which is located further towards the outer circumferential side than the inner circumferential edge 59c of the radiation cover portion 59, a safety switch is provided for detecting contact with the operator or an object when, for example, the protective cover portion 52 moves and the radiation cover portion 59 is located at the bottom, so that the internal devices of the therapeutic-radiation irradiating device 10 and so forth are not damaged.

On the side cover portions 61 and the sensor cover portion 63, safety switches are provided for detecting contact with the patient when, for example, the cover 50 rotates. Because the safety switches provided on the inner circumferential edge 59c of the radiation cover portion 59, the side cover portions 61, and the sensor cover portion 63 have different likelihoods of detecting contact between a person and an object for each amount of rotation of the cover 50, it is preferable that they be provided separately.

Furthermore, a safety switch for avoiding damaging effects on the equipment when the operator inadvertently makes contact is provided on side portions 53a of the outside cover portion 53.

Providing a safety switch in the couch 41 is preferable for detecting contact at the couch side.

The radiotherapy apparatus 3 having the configuration described above is used as follows.

First, the patient 43 is made to lie on the couch 41, and the couch 41 is moved so as to be guided into the opening 57 formed at the center of the protective cover 52. At this time, in the patient-introducing mode, the protective cover 52 is preferably moved about the central axis to position one of the side cover portions 61 at the top, as shown in FIG. 3B. By doing so, the field of view of the patient is increased and any sense of confinement is eliminated.

Next, laser light is radiated towards the affected area of the patient from a laser light source (not shown in the drawing) fixed to the ceiling of the room. The laser light source is set-up so that the laser light passes through the isocenter 19. A marker is printed on the surface of the patient's body close to the affected area. Examples of the marker include cross-shaped markers and so forth. By adjusting the position of the couch so that the laser light irradiates this marker, it is possible to roughly align the affected area of the patient with respect to the isocenter 19. At this point, the irradiation position of the laser light is visually confirmed by the operator. Because it is possible to operate the apparatus with the operator's hand placed on the flat portion 65 provided in the protective cover 52 to take some of his or her weight, the ease of use can be improved. In addition, because it is possible to use the large upper space formed by the side portion 61 which is disposed at the top, it is possible to ensure a large scanning range for the laser light.

It is also possible to substitute infrared light for the laser light. Because infrared light has a different wavelength range from the room lights, an advantage is afforded in that it is possible to align the affected area and the isocenter without turning off the room lights. In such a case, detection of the reflected light from the marker is performed by an infrared camera.

Then, using the diagnostic X-ray 35 and 36, the position of the couch 41 is controlled to align the affected area of the patient at the isocenter 19. The swinging mechanism 15 is controlled as required so that the therapeutic radiation 23 passes through the affected area.

The protective cover 52 is positioned after moving it around the central axis 18 so that the therapeutic-radiation irradiating device 16 is positioned at an irradiation angle determined according to the treatment plan. At this point, the protruding shape of the therapeutic-radiation irradiating device 16 is hidden by the opposing portion 59*a* and the neighboring portions 59*b* of the radiation cover portion 59 of the protective cover 52. As a result, the patient is not given the impression that the therapeutic-radiation irradiating portion 16 is protruding towards him or her, looming close, and therefore, the patient does not experience a sense of unease.

With the therapeutic-radiation irradiating device 16 aligned, the therapeutic radiation 23 is radiated towards the affected area from the therapeutic-radiation irradiating device 16. If the affected area, such as the lung, shifts during irradiation, the therapeutic-radiation irradiating device 16 is driven by the swinging mechanism 15 so that the therapeutic radiation 23 follows that shifting.

Once a predetermined amount of radiation is radiated, the irradiation of the therapeutic radiation 23 is stopped, and then the moving gantry 14 is moved and positioned so that the therapeutic-radiation irradiating device 16 is located at the next irradiation angle determined in accordance with the treatment plan. Then, in the same way as described above, the therapeutic radiation 23 is radiated towards the affected area.

The therapeutic radiation 23 is radiated from a desired angle by operating the rotary driving device 11 as required to rotate the support frame 12 about the rotation axis 17. By providing this rotation function, the degrees of freedom of the irradiation direction can be increased compared to the case where only the moving function of the moving gantry 14 is provided. The rotation range of the rotary driving device at this time is determined according to the position of the protective cover to avoid making contact with the patient. However, if the patient and the cover 50 unexpectedly make contact, one of the safety switches shown in FIG. 4 is activated, thus halting the operation of the radiotherapy apparatus 3.

Figure 5:
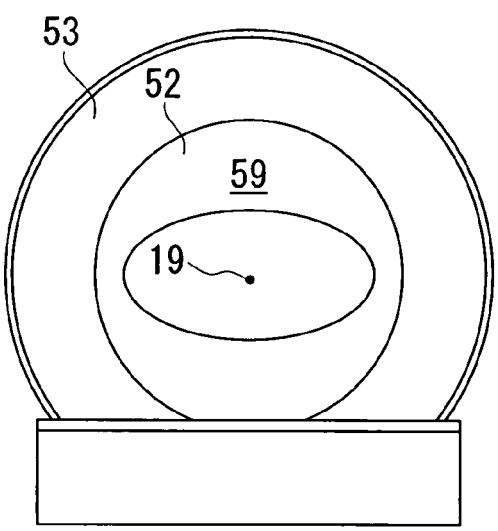
FIG. 5 is a front elevational view showing a modification of an opening provided in the protective cover.
Figure 6:
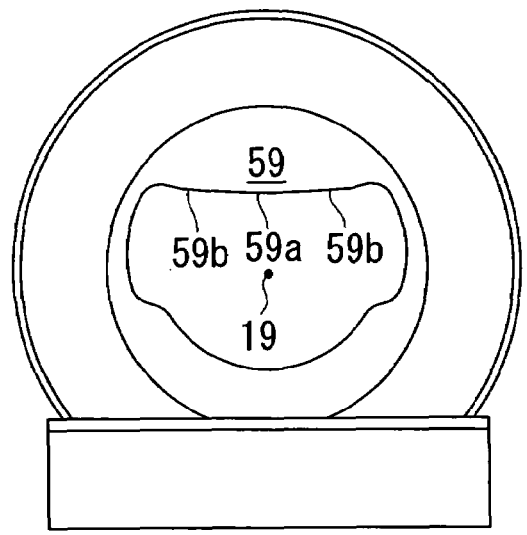
FIG. 6 is a front elevational view showing a modification of the opening provided in the protective cover.
Figure 7:
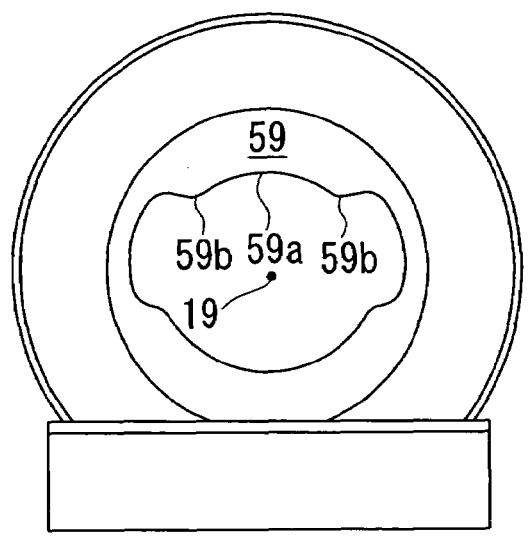
FIG. 7 is a front elevational view showing a modification of the opening provided in the protective cover.

FIG. 5 to FIG. 7 show modifications of the opening provided at the center of the protective cover 50. A shown in FIG. 5, an elliptical opening may be used. In this figure, the radiation cover portion 59 is disposed above the isocenter 19.

As shown in FIG. 6, the opposing portion 59*a* of the radiation cover 59 may have a shape that slightly projects towards the isocenter 19. Such a shape still hides the shape of the therapeutic-radiation irradiating device 16, and therefore, the patient does not experience a sense of unease.

As shown in FIG. 7, the opposing portion 59*a* may have a shape such that it is depressed more than the neighboring portions 59*b* of the radiation cover portion 59. Accordingly, the portion other than those corresponding to the diagnostic X-ray sources 24 and 25, which protrude the most towards the isocenter 19, can be depressed, which allows the sense of confinement of the patient to be eliminated.

What is claimed is:

1. A medical device, comprising:
    a substantially ring-shaped support frame provided in such a manner that a central axis through which an isocenter passes is disposed substantially horizontally;
    a substantially ring-shaped moving gantry which slides relative to the support frame and which has an opening at the isocenter side thereof;
    a radiation emitter configured to emit a beam towards the isocenter; and
    a protective cover which covers the radiation emitter and an entirety of an inner circumferential side of the moving gantry and which moves together with the moving gantry.

2. A medical device according to claim 1, wherein
    the protective cover has an opening defined by an opposing portion configured to cover the radiation emitter and side portions disposed at both sides of the opposing portion as viewed from the central axis;
    the opposing portion is disposed opposite the radiation emitter, and neighboring portions are disposed at both sides of the opposing portion as viewed from the isocenter;
    the opposing portion and the neighboring portions are arranged substantially in a straight line, or the opposing portion is arranged to be depressed more than the neighboring portions; and
    a distance from the central axis to the side portions is longer than a distance from the central axis to the opposing portion.

3. A medical device according to claim 2, wherein the side portions include flat portions.

4. A medical device according to claim 2, wherein a patient-introducing mode is provided, wherein the side portions of the protective cover are positioned in the viewing direction of a patient when the patient is introduced inside the opening of the protective cover.

5. A medical device according to one of claims 1 and 2, wherein an outside cover which is fixed to the support frame is provided at the outer side of the protective cover.

6. A medical device according to one of claims 1 and 2, wherein the protective cover is divided into at least two parts.

7. A medical device according to one of claims 1 and 2, wherein a safety switch is provided on the protective cover.

8. A medical device according to one of claims 5, wherein a safety switch is provided on the protective cover.

* * * * *